US012569403B2

(12) United States Patent
Buydts et al.

(10) Patent No.: US 12,569,403 B2
(45) Date of Patent: Mar. 10, 2026

(54) CAPSULE WITH REDUCED POWDER LEAKAGE

(71) Applicant: CAPSUGEL BELGIUM NV, Bornem (BE)

(72) Inventors: Hilde Buydts, Antwerp (BE); Kris Van Den Abeele, Asse (BE)

(73) Assignee: CAPSUGEL BELGIUM NV, Bornem (BE)

( * ) Notice: Subject to any disclaimer, the term of this patent is extended or adjusted under 35 U.S.C. 154(b) by 828 days.

(21) Appl. No.: 17/782,067

(22) PCT Filed: Dec. 3, 2020

(86) PCT No.: PCT/EP2020/084494
§ 371 (c)(1),
(2) Date: Jun. 2, 2022

(87) PCT Pub. No.: WO2021/110849
PCT Pub. Date: Jun. 10, 2021

(65) Prior Publication Data
US 2023/0017517 A1     Jan. 19, 2023

(30) Foreign Application Priority Data

| Dec. 5, 2019 | (EP) | ..................................... | 19213991 |
| Jan. 28, 2020 | (EP) | ..................................... | 20154179 |
| Feb. 14, 2020 | (EP) | ..................................... | 20157494 |
| Jul. 6, 2020 | (EP) | ..................................... | 20184127 |

(51) Int. Cl.
*A61J 3/07*     (2006.01)
*A61K 9/48*     (2006.01)

(52) U.S. Cl.
CPC ............. *A61J 3/071* (2013.01); *A61K 9/4816* (2013.01)

(58) Field of Classification Search
None
See application file for complete search history.

(56) References Cited

U.S. PATENT DOCUMENTS

2007/0036830 A1     2/2007   Vanquickenborne et al.

FOREIGN PATENT DOCUMENTS

| DE | 2232236 A1 | 1/1974 |
| FR | 2780648 A1 | 1/2000 |
| WO | 9717049 A1 | 5/1997 |
| WO | WO 2009/007377 | * | 1/2009 |
| WO | 2009138920 A1 | 11/2009 |

OTHER PUBLICATIONS

English translation of WO 2009/007377 (Year: 2024).*
Kousouretas, Ioannis (Authorized Officer), International Search Report and Written Opinion dated Feb. 22, 2021 for International Patent Application No. PCT/EP2020/084494, 12 pages.

* cited by examiner

*Primary Examiner* — Bennett M Celsa
*Assistant Examiner* — Garen Gotfredson
(74) *Attorney, Agent, or Firm* — MH2 Technology Law Group, LLP

(57) ABSTRACT

The present invention relates to a capsule shell with two parts, a cap and a body, the two parts engage telescopically with each other, the capsule shell is used for storing solid substances in powder or granular form and shows a minimized leakage rate of powder when the capsule shell is filled with the solid substances in powder form and is closed.

31 Claims, 9 Drawing Sheets

CAPSULE WITH REDUCED POWDER LEAKAGE

CROSS-REFERENCE TO RELATED APPLICATIONS

This application is a U.S. National Stage application of PCT/EP2020/084494 filed 3 Dec. 2020, which claims priority to European Patent Application No. 19213991.3 filed 5 Dec. 2019, European Patent Application 20154179.4 filed 28 Jan. 2020, European Patent Application No. 20157494.4 filed 14 Feb. 2020, and European Patent Application No. 20184127.7 filed 6 Jul. 2020, the entire disclosures of which are hereby incorporated by reference in their entireties.

FIELD OF THE INVENTION

The present invention relates to a capsule shell with two parts, a cap and a body, the two parts engage telescopically with each other, the capsule shell is used for storing solid substances in powder or granular form and shows a minimized leakage rate of powder when the capsule shell is filled with the solid substances in powder form and is closed.

BACKGROUND OF THE INVENTION

Standard containers for pharmaceutical or other substances in solid form may be capsule shells which have two parts, a cap part, also called cap, and a body part, also called body. The cap and the body telescopically engage with each other for closing the capsule shell.

WO 97/17049 A1 discloses in FIG. 1 such a telescope-type capsule shell with these two telescopically engaging parts, cap and body. The body of a capsule has an airvent. Furthermore, the body has a ring closure protrusion extending circumferentially around the body. Adjacent to the section with the ring closure protrusion the body extends toward its closed end in a hollow-cylindrical shape. The airvent extends from the edge of the open end of the body over the full length of the section of the body with the ring closure protrusion and extends into the section which has the hollow-cylindrical shape. The cap has essentially a hollow-cylindrical shape expect for the dome shaped closed end. The cap has individual protrusions with oval shape around it circumference in the section of the cap with the hollow-cylindrical shape. These protrusions interact with the ring closure protrusion of the body in the preclosed position. The section itself that carries these oval shaped protrusions shows no further indentation, so the area between the protrusions has the same diameter as the rest of the hollow-cylindrical section of the cap.

A disadvantage of the disclosed capsule shell is a certain leakage rate when it is filled with a solid substance in form of a powder.

There was a need for a telescope-type capsule shell with these telescopically engaging two parts, cap and body, which shows reduced leakage rates.

The invention relates to a specific design of the cap and the body for reducing the leakage rate of powder substances contained within the capsule shell.

SUMMARY OF THE INVENTION

Subject of the invention is a telescope-type capsule shell, CAPSSHELL, with two separate parts, a cap and a body, wherein the cap and the body telescopically engage with each other for closing CAPSSHELL;

the cap has a closed end, CEC (20), and an open end;
the body has a closed end, CEB (10), and an open end;
the cap comprises four consecutive segments SC0, SC1, SC2 and SC3;
SC0 comprises CEC (20);
SC1 comprises a closure ring of the cap, CRC, in form of a protrusion that extends over the entire circumference of the cap;
SC2 comprises a region of protrusion of the cap, RPC;
SC3 comprises the rim of the open end of the cap, RIC;
the body comprises four consecutive segments SB0, SB1, SB2 and SB3;
SB0 comprises CEB (10);
SB1 comprises a hollow-cylindrical segment of the body, CSB;
SB2 comprises a closure ring of the body, CRB, in form of a protrusion that extends over the entire circumference of the body;
SB3 comprises the rim of the open end of the body, RIB;
in the RPC there are at least two protrusions, PRPC, which are separated from each other in the circumferential direction of the cap by parts of RPC;
a closed position is the position where the cap is fully engaged with the body so that CASPSHELL is closed,
in the closed position CRC engages with CRB;
any protrusion of CAPSSHELL extends inwardly into the cavity of the cap or the body, respectively;
the extension of the CAPSSHELL, when the cap is telescopically engaged with the body in the direction of its length is designated as x direction;
characterized in that
in the RIB there are at least two airvents, AV, in form of protrusions, which are separated from each other and which extend from the edge of the open end of the body, EB, to CRB;
and
the RPC extends over the entire circumference of the cap.

Abbreviations

The following abbreviations are used in this specification:
API active pharmaceutical ingredient
AV airvent
CAPSSHELL capsule shell
CEB closed end of the body
CEC closed end of the cap
CMC carboxymethyl cellulose
CRB closure ring of the body
CSB hollow-cylindrical segment of the body
CRC closure ring of the cap
DAV between the lowest point of the outer surface of an indentation formed by an AV and the outer surface of the diametrical opposite point of the wall of the RIB
DCRB diameter between two diametrically opposing points of the outer surface of the CRB with the largest depth of the indentation formed by CRB
DCRC diameter between two diametrically opposing points on the inner surface of the CRC at the longitudinal point of largest depth of the indentation formed by CRC
DRPC diameter between two diametrically opposing points on the inner surface of the RPC at the point of largest depth of the indentation formed by the RPC, that is the lowest point of the inner surface of the RPC in x direction, except for any area formed by the PRPC
D-CEC-CRC inner diameter of CEC and CRC at the transition between CEC and CRC D-CRC-RPC inner diameter of CRC and RPC at the transition between CRC and RPC D-RPC-RIC inner diameter of RPC and RIC at the transition between RPC and RIC DIPSOL solution of FILMPOLYM in water DISSOL dissolution of FILMPOLYM in water DPRPC diameter between the lowest point of the inner surface of an indentation formed by the PRPC and its diametrically opposing point of the inner surface of the wall of the cap EB edge of the open end of the body, which is the cutting edge of the RIB EC edge of the open end of the cap, which is the cutting edge of the RIC FILLFORMUL formulation filled into CAPSSHELL FILMCOMP composition of the capsule film FILMPOLYM film-forming polymer FURTHERSUBST further substances optionally comprised in FILMCOMP HPMC hydroxypropyl methylcellulose ICRC interference between the lowest point of the inner surface of the indentation formed by CRC and the outer surface of the body, where the body has its largest diameter, preferably the MDB IDPRPC interference between the lowest point of the inner surface of the indentation formed by the PRPC and the outer surface of the body, where the body has its largest diameter, preferably the MDB INGR ingredient in FILLFORMUL MDB maximum outer diameter of the body MDC maximum inner diameter of the cap PINTEMP temperature of the mold pin PLF prelock force PROCFORMCAPS process for the method for preparation of CASPSHELL PRPC protrusion in the RPC RIB rim of the open end of the body RIBC segment of RIB towards the closed end of the body RIBO segment of RIB towards the open end of the body RIC rim of the open end of the cap RPC region of protrusion of the cap SB0, SB1, SB2, SB3 segments of the body SC0, SC1, SC2, SC3 segments of the cap SFF snapfit force

DETAILED DESCRIPTION OF THE INVENTION

By providing at said least two AVs in the RIB which extend from the EB to the CRB, but not over the entire length of the CRB into the CSB, and by providing the RPC extending over the entire circumference of the cap, and by providing PRPC in the RPC, the leakage rate is reduced.

Any AV in the RIB extends from the EB to the CRB, but not over the entire length of the CRB into the CSB. Any AV ends at or in the CRB. The CSB does not contain an AV or any part of an AV. If an Av would protrude into the CSB then this would result in an opening in the closed position which may result in powder leakage.

Telescopic engagement in the sense of this invention means an at least partial contact of the inner wall of the cap with the outer wall of the body. It also means that cap and body, where they overlap in the closed position, show an at least partial fit of their forms. The telescopic engagement of the cap and the body may be realized by sliding the cap over the body, in other words by inserting the body into the cavity of the cap. The body is slid with the open end first into the cavity of the cap. Thereby the cap and the body are at least partially form fittingly connected or engaged. So telescopic engagement means am at least partial form fitting engagement of the cap with the body.

In the closed position CAPSSHELL may have an essentially hollow-cylindrical shape.

In the closed position the telescopic engagement of the cap with the body may extend over SC1, over SC2 and over SC3 of the cap and over SB3, over SB2 and over SB1 or at least over a part of SB1 of the body.

A preclosed position of CAPSSHELL is the position wherein the cap is telescopically only partly engaged with the body. CASPSHELL is not yet closed in the preclosed position.

The extension of the CAPSSHELL, when the cap is telescopically engaged with the body, for example in the closed or in the preclosed position, in the direction of its length may be designated as x direction or as longitudinal direction. Similarly the length of the cap and the length of the body refers to their lengths in x direction. So the term length is used to designate a length in x direction The length of the cap extends in x direction from the edge of the open end of the cap, EC, to the end of the CEC. The length of the body extends in x direction from the EB to the end of the CEB.

Width in the sense of the invention signifies a direction along the circumference of the cap or the body, respectively.

Any protrusion in the sense of this invention is any kind of indentation or recess, regardless of its shape, that extends inwardly into the direction of the cavity of the cap or the body, respectively. The inward direction may be perpendicular to the surface of the wall. By the protrusion an indentation or recess in the wall of the cap or the body, respectively, is formed when the protrusion is viewed from the outside of the cap or the body, respectively.

Depth in the sense of the invention signifies a direction from the outer surface into the cavity of the cap or the body. The direction of depth may be perpendicular to the surface of the cap or the body.

The maximum inner diameter of the cap, MDC, may be the largest inner diameter of the RIC. The maximum outer diameter of the body, MDB, may be the largest outer diameter of the RIB.

In the sense of the invention, any diameter of the cap refers to an inner diameter, that is to a diameter of two diametrically opposing point of the inner surface of the cap, if not explicitly stated otherwise.

In the sense of the invention, any diameter of the body refers to an outer diameter, that is to a diameter of two diametrically opposing point of the outer surface of the body, if not explicitly stated otherwise.

During or after telescopic engagement of the body and the cap an interference between the body and the cap occurs.

Interference in the sense of the invention means that the diameter of two diametrically opposing points of the inner surface of the cap is smaller than the respective diameter of the corresponding diametrically opposing points of the outer surface of the body when CAPSSHELL is closed or preclosed, that is when cap and body are in closed or preclosed position.

Interference may also occur during the telescopic engagement of the cap with the body, then it means that the diameter between two diametrically opposing points of the inner surface of the cap is smaller than the MDB, the MDB may be the largest outer diameter of the RIB. When the cap is telescopically engaged with the body this interference creates a tension in the radial direction and thereby a force needs to be applied during the sliding of the cap over the body.

Interference causes a deformation of the cap and/or the body at the point where interference occurs.

A force is required to deform the wall of the cap and/or body at the point and/or over the path where the interference occurs during the telescopic engagement of the cap and the body, that is during the sliding of the cap over the body.

Interference in the closed or preclosed position means that the engagement of the cap with the body is a force fit engagement.

The open position of CAPSSHELL is any position of its cap and body where the cap and the body are separated from each other and any telescopic engagement of the cap with the body has not yet started. The telescopic engagement of the cap with the body starts when the cap approaches the body from the open position in x direction and the edge of the open end of the cap EC comes into alignment with the edge of the open end of the body EB in the x direction.

In the preclosed position the telescopic engagement of the cap with the body may extend over a part of SC1, over SC2 and over SC3 of the cap and over SB3, over SB2 and over a part of SB1 of the body.

In one embodiment A of CAPSSHELL, PRPC engage in the preclosed position with CSB. In the preclosed position CRC is on the other side of RIB with respect to CRB, that is CRC is on the open end side of RIB. The PRPCs are arranged in the RPC at a distance in x direction from the position of the smallest diameter of the CRC which distance is larger than the distance in x direction between the EB and the end of the CRB adjacent to the CSB.

In another embodiment B of CAPSSHELL, PRPC engage in the preclosed position with CRB. In the preclosed position CRC is on the other side of RIB with respect to CRB, that is CRC is on the open end side of RIB. The PRPCs are arranged in the RPC at a distance in x direction from the position of the smallest diameter of the CRC which distance equals the distance in x direction between the EB and the position of the smallest diameter of the CRB.

During telescopic engagement of the cap and the body, in particular when bringing the body and cap from the preclosed position to the open position, a prelock force, PLF, has to be applied. The PLF is the force which is necessary to move the cap from the preclosed position to the open position; preferably it is the largest force that occurs during the movement of the cap from the preclosed position to the open position.

A snapfit force, SFF, is the force which is necessary to move the cap from the closed position to the open position; preferably it is the largest force the occurs during the movement of the cap from the closed position to the open position.

PLF is preferably smaller than SFF. PLF may be from 0.1 to 0.2 N. SFF may be from 3 to 6 N.

The PLF may be caused by an interference occurring during the telescopic engagement of the cap with the body The SFF may be caused by an interference occurring during the telescopic engagement of the cap with the body The main part of the cap may have a hollow-cylindrical shape; this pertains essentially to the SC3, SC2 and SC1.

The RIC may have a length of from 0 to 20%, preferably from 5 to 15%, of the length of the cap. When the RIC has a length of 0% of the length of the cap, then MC actually is the EC. When the RIC has a length of greater than 0% of the length of the cap, then its surface may be flat and may be part of or may contribute to the hollow-cylindrical shape of the cap.

The RPC forms an indentation in the wall of the cap which extends into the cavity formed by the cap. This indentation extends over the entire circumference of the cap. The RPC may have a length of from 30 to 40%, preferably of from 33 to 40%, of the length of the cap. The shape of a longitudinal cut in x direction of the indentation that the RPC forms may be a curved shape, preferably a concave curved shape, in particular a concave shape forming part of an oval, or a shape of a tub with a flat bottom and round slopes. The shape of a longitudinal cut in x direction of the indentation that the RPC forms may for example have a U shape or a V shape, preferably a U shape.

RPC has a smaller inner diameter than the MDC, the reduction of the diameter between two diametrically opposing points on the inner surface of the RPC at the point of largest depth of the indentation formed by the RPC, that is the lowest point of the inner surface of the RPC in x direction, except for any area formed by the PRPC, may be from 0.5 to 2% of the MDC, so the diameter, DRPC, between two diametrically opposing points on the inner surface of the RPC at the point of largest depth of the indentation formed by the RPC, that is the lowest point of the inner surface of the RPC in x direction, except for any area formed by the PRPC, may be from 98 to 99.5% of the MDC. Preferably said lowest point of the inner surface of the RPC extends over the entire circumference of RPC; thereby said lowest point actually is a line, preferably said lowest point actually is a straight line forming a ring; this is preferably the case when the shape of a longitudinal cut in x direction of the RPC may has a U shape or a V shape, preferably a U shape. The maximum depth of the indentation formed by the RPC may be from 10 to 40 micrometer.

Between the RPC, except for any area formed by the PRPC, and the circumference of the body with MDB there occurs no interference during the telescopic engagement of the cap with the body, that is during the sliding of the cap over the body. That means that DRPC is equal to or larger than MDB. The depth of the gap formed between RPC and the point of the body with the MDB is called clearance and may be expressed by (DRPC−MDB)/2. The range of the clearance may be from 0 to 50 micrometers, preferably from 0 to 20 micrometer, and this clearance may extend consecutively up to 80%, preferably up to 70%, of the length of the RPC. So the RPC may be shaped for example in form of a concave shaped depression over its length, in this case the clearance exists only at the point of largest depression of the concave shaped RPC, or the RPC may be shaped over its length with three consecutive segments, a first segment with an inclination creating the depression, a second segment, the middle segment, with no inclination, creating a flat bottom, and a third segment with in inclination to remove again the depression. In this case the clearance extends over the length of the second segment.

The RPC, the clearance and their defined sizes and geometries, for example their lengths, contribute to reducing the leakage rate. It is assumed that particles may stick between the cap and the body while the cap is slid over the body, especially when the clearance between the cap and the body is to large. By particles which are sticking in the clearance during the sliding of the cap over the body the gap between the cap and body may be enlarged and may be still present even in the closed state; thereby powder may leak through this gap. By having a rather small and defined clearance the chances are reduced that particles stick between the cap and the body. The RPC creates the reduced and defined gap between the cap and the body edge during final closing after filling of the capsule, this is an important parameter to prevent powder leakage for example for powders with large particle distribution. For this reason the RPC needs to extend over the entire circumference of the cap.

If between the RPC, except for any area formed by the PRPC, and the circumference of the body with MDB there would occur an interference during the telescopic engagement of the cap with the body, that is during the sliding of the cap over the body, then the air would be prevented or at least would have difficulties to escape while the cap slides over the body, thereby the closing of the capsule is made more difficult or even impossible; the cap may no longer rest on the body in the preclosed or closed position but the capsules may snap open by the elevated pressure in the capsules created by the air that has not escape while closing, but which was compressed while closing the capsule.

The PRPC are indentations in the RPC. The diameter between the lowest point of the inner surface of an indentation formed by the PRPC and its diametrically opposing point of the inner surface of the wall of the cap may be called abbreviated DPRPC; said diametrically opposing point of the inner surface of the wall of the cap may be a point on the inner surface of RPC or a point of the inner surface of PRPC. DPRPC may be from 96 to 99%, preferably from 97 to 99%, of the MDC.

The indentation of the PRPC extend so far into the cavity formed by the cap that there occurs an interference, IDPRPC, during the telescopic engagement of the cap with the body between the lowest point of the inner surface of the indentation formed by the PRPC and the outer surface of the body, where the body has its largest outer diameter, preferably the MDB, which may be the RIB. So an interference may occur between the PRPC and RIB during the telescopic engagement of the cap with the body. Between the PRPC and the circumference of the body with MDB there may occur an interference during the telescopic engagement of the cap with the body.

Preferably the shape of the PRPC and the depth of the indentation formed by the PRPC are the same for each PRPC, that means all the PRPCs are identical in shape and depth. Preferably the area of the PRPC has an oval shape with from equal length and width to larger length than width. Preferably the length of PRPC is smaller than the length of RPC. Preferably the width of the PRPC is from 80 to 100%, more preferably 82 to 90%, of their length. Preferably the length of the PRPC is from 20 to 30%, more preferably 22 to 27%, of the length of the RPC. The maximum depth of the indentation formed by the PRPC may be from 60 to 80 micrometer.

IDPRPC may be expressed by (MDB−DPRPC)/2 and may be from 10 to 50 micrometer, preferably from 20 to 40 micrometer. IDPRPC may contribute to the PLF and/or to the SFF.

The RPC may have, for example, 2, 3, 4, 5, 6, 7, 8, 9 or 10 PRPCs; preferably 4, 5, 6, 7, or 8; more preferably 4, 6 or 8, even more preferably 6 PRPCs. Preferably the PRPCs are separated from each other by parts of RPC with equal width, that means that the PRPCs are placed with equal distance from each other over the circumference of the RPC. In one embodiment, the RPC may have an even number of PRPCs. The PRPC may be placed in such a way that always two PRPC form a pair that are located on diametric opposite sides of the PRC.

Preferably, the PRPCs are separated in x direction from the beginning and the end of RPC by parts of RPC; that means the PRPC do not extend to the beginning of RPC nor to the end of RPC. Preferably, all the PRPCs have the same distance from RIC in x direction. In one particular embodiment the PRPCs are located in the quarter of the length extension of the RPC closest to the RIC. In another particular embodiment the centers of the PRPCs are located at from 35 to 65% of the length of the RPC from the beginning of the RPC on the side of the RIC, preferably at the middle of the length of the RPC.

The PRPC and the IDPRPC caused by the geometry of the PRPC, such as the depth of the PRPC and also their size, that is for example the length and the width of the PRPC, in relation to the geometry of the RPC, are facilitate keeping the cap in the preclosed position. The PLF is strongly influenced by the geometry of the PRPC. Without PRPC the cap easily falls from the body when the cap sits in the preclosed position on the body, which needs to be prevented in any handling of empty capsules, such as during and filling operations in filling machines, or during any application of printing on capsules etc., since the empty capsules are handled prior to the filling step itself with the cap sitting on the body in the preclosed position, and the cap needs to stay in this preclosed position in any handling steps before the actual filling and closing. But on the other side the PLF must not be too high, because the filling machine, once the capsules in the preclosed position have been filled into the filling machine, at first opens the capsules by removing the cap from the body, and for this removal the PLF must not be too high otherwise the filling machine may no longer be capable to open the capsules, that is to remove the cap from the body, and such an unopened capsule is a wasted capsule in the filling process. The PRPC, its geometry, and the IDPRPC caused by the geometry of the PRPC, such as the depth of the PRPC and also their size, that is for example the length and the width of the PRPC, in relation to the geometry of the RPC, are also essential for reducing the leakage rate or for keeping the leakage rate at a low level, because if the interference caused by the PRPC is too big than again the gap, that is the clearance between the RPC and the body, while the cap slides over the body, is enlarged and becomes too big and particles may again stick between the cap and the body while the cap slides over the body, thereby the desired reduction of leakage rate caused by the optimization of the clearance by the chosen geometry of the RPC as described would be offset. For this reason the embodiment A is preferred over embodiment B, since the PRPC in the preclosed position in embodiment A engage already with the CSB and are no longer located in the region of the CRB, so when the capsule has been filled and is being closed by moving the cap from the preclosed to the closed position, the clearance between the RPC and the body will in embodiment A be less influenced by any interference of PRPC with the body then in embodiment B.

The CRC may have a length of from 13 to 23%, preferably from 13 to 20%, more preferably from 13 to 17%, of the length of the cap. The CRC forms an indentation of the wall of the cap into the cavity formed by the cap. The diameter, DCRC, between two diametrically opposing points on the inner surface of the CRC at the point of largest depth of the indentation formed by CRC, that is the lowest point of the inner surface of the CRC in x direction, is from 95 to 97.5% of MDC. Preferably this lowest point of the inner surface of the CRC extends over the entire circumference of CRC; thereby said lowest point actually is a line, preferably a straight line forming a ring. DCRC may be equal or smaller than DRPC, preferably smaller.

DCRC may be equal or smaller than DPRPC, preferably smaller.

The shape of a longitudinal cut in x direction of the CRC may have a curved shape, preferably a concave curved shape, it may have an U shape or a V shape, this is preferably the case when said lowest point actually is a straight line forming a ring; preferably a V shape.

During the telescopic engagement of the cap with the body an interference, ICRC, occurs between the lowest point of the inner surface of the indentation formed by CRC and the outer surface of the body, where the body has its largest outer diameter, preferably the MDB, which may be the RIB. ICRC contributes to the SFF. So ICRC may occur between CRC and RIB during the telescopic engagement of the cap with the body. ICRC may be from 60 to 100 micrometer.

In the closed position, CRC may engage with CRB also with an interference; the interference may be from 20 to 40 micrometer.

In the closed position the PRPCs may engage with CSB.

In one embodiment the cap has only one closure ring, CRC.

In one embodiment, the body has only one closure ring, CRB.

When the cap has only one closure ring, CRC, and the body has only one closure ring of the body, CRB, these two closure rings are complementary to each other in the closed position.

When the cap has only one closure ring, CRC, and the body has only one closure ring of the body, CRB, then this one closure ring, CRC, of the cap engages in the closed position with this one complementary closure ring of the body, CRB.

In one embodiment the regions CSB and CEB of the body do not have an inwardly extending protrusion in form of a circumferential ring, preferably the regions CSB and CEB of the body do not have any inwardly extending protrusion, more preferably the region CSB of the body has a continuously and circumferentially flat surface without any protrusions.

CEC may have a length of from 30 to 45%, preferably from 30 to 40% of the length of the cap. CEC may have any form. In one embodiment CEC is dome shaped.

The inner diameter of CEC and CRC at the transition between CEC and CRC may be the identical diameter, D-CEC-CRC, that is CEC and CRC transition from one to the other without a step wise change of diameter.

The inner diameter of CRC and RPC at the transition between CRC and RPC may be the identical diameter, D-CRC-RPC, that is CRC and RPC may transition from one to the other without a step wise change of diameter.

The inner diameter of RPC and RIC at the transition between RPC and RIC may be the identical diameter, D-RPC-RIC, that is RPC and RIC may transition from one to the other without a step wise change of diameter.

Between the transition between CRC and RPC and the transition between RPC and RIC the indentation formed by RPC occurs, that is the diameter between the transition between CRC and RPC and the transition between RPC and RIC is reduced with respect to the diameters D-CRC-RPC and D-RPC-RIC.

D-CEC-CRC, D-CRC-RPC and D-RPC-RIC may be identical, they may be identical to MDC.

The main part of the body may have a hollow-cylindrical shape; this pertains essentially to the SB1, SB2 and SB3.

The hollow-cylindrical shape of the main part of the body may have a taper, wherein the diameter of the main part of the body at the closed end of the body is smaller than the diameter of the main part of the body at the open end of the body. Preferably the taper of the main part of the body extends at least over SB1, more preferably over CSB. If the hollow-cylindrical part of the body has a taper, it may also be referred to as a hollow-conical part of the body. So in sense of the invention hollow-cylindrical encompasses also hollow-conical.

Preferably, any taper of the hollow-cylindrical part of the body is so small that still the impression of an essentially hollow-cylindrical shape of CAPSSHELL in the closed position is maintained.

The RIB may have a length of from 4 to 8% of the length of the body.

In one embodiment, the diameter of the RIB may be the same over the length of the RIB.

In another embodiment, the RIB has two adjacent segments over its length, one segment, RIBO, towards the open end of the body and one segment, RIBC, towards the closed end of the body. Where RIBO and RIBC transition from one to the other, the outer diameters of RIBO and RIBC may be the same, so there may be no stepwise change of the outer diameter at the transition from RIBO to RIBC. RIBO may have a taper by which the diameter of RIB is reduced over the length of the RIBO towards EB; thereby EB has a smaller diameter than RIBC. This facilitates the alignment of the cap with the body and the beginning of the telescopic engagement of the cap with the body when the cap is slid over the body.

In one embodiment, RIBC may have the same diameter over its length. Preferably, the diameter of RIBC is the same diameter as the diameter of CSB at its end towards the open end of the body.

In another embodiment, RIBC may have a taper which reduces it diameter in direction to the closed end of the body. This is preferably the case when also the main part of the body, in particular CSB, has a respective taper reducing the diameter of CSB in the direction to the closed end of the body. Preferably, the taper of RIBC may be the same taper which the main part of the body, in particular CSB, has. Preferably, the diameter of RIBC and its change by the taper in the direction towards the open end of the body is an extension of and corresponds to the change of the diameter of CSB towards the open end of the body. Thereby the tapered surface of RIBC is an extension of the tapered surface of the CSB.

The RIB may have, for example, 2, 3, 4, 5, 6, 7, 8, 9, 10, 11 or 12 AVs, preferably 4, 5, 6, 7, 8, 9, 10, 11 or 12 AVs, more preferably 6, 7, 8, 9, 10, 11 or 12 AV, even more preferably 6, 7, 8, 9, 10 or 11 AVs, especially 6, 7, 8, 9 or 10 AVs. In one embodiment, the RIB may have an even number of AVs, preferably 4, 6, 8, 10 or 12 AVs, more preferably 6, 8 or 10 AVs, even more preferably 8 AVs.

Preferably, the AVs are separated from each other by parts of RIB, more preferably by parts of RIB with equal width. This means that more preferably the AVs are placed with equal distance from each other over the circumference of the RIB; respective parts of RIB are in between the AVs and separating thereby each AV from the neighboring AV. The AVs may be placed in such a way that always two of the AVs form a pair that are located on diametrical opposite sides of the RIB; preferably the number of AVs is an even number.

The AVs are indentations in the RIB. The indentations caused by the AVs reduce the diameter of RIB. The diameter, DAV, between the lowest point of the outer surface of an indentation formed by an AV and the outer surface of the diametrical opposite point of the wall of the RIB may be from 99 to 99.9%, preferably 99.2 to 99.8%, even more preferably from 99.3 to 99.7%, especially from 99.4 to 99.7%, of the MDB.

Preferably the shape of the area of the AV and the depth of the indentation formed by the AV are the same for each AV, that means all the AV are identical, that means the shape and the depth of all of the AVs are identical.

When RIB has no taper then the longitudinal cross section of the AV may have a rectangular shape. When RIBC or RIBO has a taper then the longitudinal cross section of the AV may have a rectangular shape over the length of the region or regions where RIB has no taper and may have a respective trapezoidal shape over the length of the region or regions where RIB has a taper; when both RIBC and RIBO have a taper than the respective parts of the AV may have a respective trapezoidal shape.

The length of the AVs is the same as the length of the RIB. Thereby, the AVs extends from the EB to the CRB. Preferably the outer diameter of the CRB at the transition from the RIB to the CRB is the same as the outer diameter of the RIB at this transition, that means the outer diameter does not make a step wise change at the transition between the RIB and the CRB. Since the CRB is a protrusion into the cavity of the body with respect to the RIB, the AVs extend into the beginning of the CRB according to their depth: The AVs extend into the CRB until the point where the depth of the protrusion of the AV is equal to the depth of the protrusion of the CRB. The AV does not extend to the CSB.

Preferably the maximum width of the AVs is same or smaller than the length of AVs, preferably the width of AVs is from 85 to 100%, more preferably from 90 to 100% of the length of AV.

Preferably the lowest point of the surface of the AVs extends over the full length of AVs; thereby said lowest point actually is a line, preferably a straight line, which extends in the x direction.

Preferably the surface of the area of the AVs is flat.

In order to reduce the leakage rate, the AV do not have a huge depth but are rather shallow, so the size of DAV is closed to the size of MDB. When the AV are rather shallow it is preferred that the RIB has more than the usual 2 AV which are commonly encountered with commercial capsules, the preferred number of AV is as given herein. The higher number of AV facilitates that even with rather a shallow depth of the AV the air will still be able to escape when the cap is sliding over the body during closure of the capsule. Furthermore is it preferred for reducing the leakage rate in combination with an optimum of PLF to have more than 2 PRPC on the RIB, the preferred number of PRPC is as given herein. To have a number of PRPC which different from the number of AV, and not an equal number together with an equal circumferential distribution of PRPC and of AV, is beneficial to ensure that the PRPC will not be able to have the same circumferential position on the RPC as the AV have on the RIB, which would make it possible that the PRPC actually slide through the AV while the cap slides over the body; this would result in a higher variation of PLF: lower PLF when the cap and the body is aligned in such a way that the PRPC slide through the AV, and higher PLF when the PRPC are not circumferentially aligned with the AV and therefore do not slide through the AV while the cap slides over the body. As it is not practical to align the cap and the body into a defined relative position to each with respect to the circumferential position of the PRPC and of the AV during the filling process, for example in a filling machine, but rather the circumferential alignment for the cap relative to the body during filling, for example in a filling machine, is arbitrary and may vary from capsule to capsule, it is better to have a number of PRPC which is different from the number of AV, and preferably as mentioned herein, the AVs and the PRPCs are separated from each other by parts of RIB and by parts of RPC respectively with respective equal widths. This means that preferably the AVs and the PRPCs are placed with respective equal distance from each other over the circumference of the RIB and of the RPC respectively. Thereby the possible variation of the PLF is reduced, as in this setting, equal distance between each AV and between each RPC respectively, but unequal number of PRPC and of AV, it is not possible that all PRPC are aligned circumferentially with an AV, but always at least one PRPC is not aligned circumferentially with an AV and does not slide through an AV when the cap slides over the body. One such embodiment of a cap and a body has the combination of 8 AV and 6 PRPC.

The CRB forms an indentation of the wall of the body into the cavity formed by the body.

The CRB may have a length of from 4 to 8% of the length of the body. The diameter, DCRB, between two diametrically opposing points of the outer surface of the CRB at the point of largest depth of the indentation formed by CRB, that is the lowest point of the outer surface of the CRB in x direction, is from 90 to 98%, more preferably from 92 to 98%, even more preferably from 94 to 98%, especially from 96 to 98%, more especially from 97.5 to 98%, of MDB. Preferably this lowest point of the outer surface of the CRB extends over the entire circumference of CRB; thereby said lowest point actually is a line, preferably a straight line forming a ring.

Preferably the diameter of the CRB and the diameter of the RIB are equal at the transition from the CRB to the RIB. That means there is not step wise change of diameter at the transition from the CRB to the RIB.

Preferably the diameter of the CSB and the diameter of the CRB are equal at the transition from the CSB to the CRB. That means there is not step wise change of diameter at the transition from the CSB to the CRB.

Preferably the diameter of the CRB is reduced without a step wise change starting from the transition of the CRB to the RIB in the direction to the end of the body until it reaches the point with the largest depth of the indentation formed by CRB, and then it increase again without a step wise change from this lowest point in the direction to the end of the body until it reaches the transition from the CRB to the CSB.

Preferably, the shape of a longitudinal cut in x direction of the CRB may have a curved shape, preferably a concave curved shape, it may have an U shape or a V shape, this is preferably the case when said lowest point actually is a straight line forming a ring; preferably a U shape.

The combined lengths of CSB and CEB may be from 85 to 90% of the length of the body.

Optionally CSB may have a protrusion or protrusions corresponding to PRPC which engage with PRPC in the closed position. Said protrusion may be a ring in form of an indentation that extends over the entire circumference of the body. Preferably said engagement is without interference between the PRPC and this optional protrusion.

CEB may have any form. In one embodiment CEB is dome shaped.

Preferably, the cap has four consecutive segments SC0, SC1, SC2 and SC3.

Preferably, the body has four consecutive segments SB0, SB1, SB2 and SB3.

Preferably,
SC0 is the CEC;
SC1 is the CRC;
SC2 is the RPC;
SC3 is the RIC.
Preferably,
SB0 is the CEB;
SB1 is the CSB;
SB2 is the CRB;
SB3 is the RIB.

The cap and the body of CAPSSHELL may each be formed by an elastic wall. The elasticity provides for avoiding any fracture of the cap and/or the body during telescopic engagement of the cap with the body, especially when interference occurs.

CASPSHELL is made of a capsule film which has a composition, FILMCOMP, comprising a film-forming polymer, FILMPOLYM, ordinarily used for a capsule film, such as cellulose derivative, gelatin, pullulan and soluble starch or a soluble starch derivative.

The typical wall thickness of CAPSSHELL, that is the wall thickness of the capsule film, is known to the skilled person, a typical value may be 100 or 105 micrometer, a typical range may be from 90 to 110 micrometer.

Typical sizes of CAPSSHELL are known to the skilled person and may be for examples expressed in the sizes as disclosed in the Technical Reference File Hard Gelatin Capsules, 2nd Edition, Capsugel Library, www.capsugel-.com. Example for the sizes are 000, 00, 0, 1, 2, 3, 4 or 5.

So FILMCOMP is the composition of CASPSHELL, of the cap, of the body, that is of the wall that forms CAPSSHELL, the cap and the body, respectively.

The cellulose derivative may be hypromellose (hydroxypropyl methylcellulose, HPMC). Examples HPMC include HPMC2910 containing about 29% of a methoxy group and about 10% of a hydroxypropoxyl group; HPMC2906 containing about 29% of a methoxy group and about 6% of a hydroxypropoxyl group; and HPMC2208 containing about 22% of a methoxy group and about 8% of a hydroxypropoxyl group.

The polymer may be used singly or as a mixture.

CAPSSHELL may be a hard or soft capsule shell, preferably a hard capsule shell.

CAPSSHELL may comprise water. The water stems from the production process which is using an aqueous composition for preparing CAPSSHELL, so the water in CAPSSHELL is typically residual water remaining in CAPSSHELL after drying. Typical content of water in CAPSSHELL is 25 wt % or less, preferably 20 wt % less than, more preferably from 0 to 14 wt %, even more preferably from 1 to 14 wt %, especially from 2 to 14 wt %, more preferably from 3 to 14 wt %, of water, the wt % being based on the weight of the CAPSSHELL FILMCOMP may comprise further substances, FURTHERSUBST, such as selected from the group consisting of salt, additive such as a gelling agent, gelling aid, plasticizer, pH regulator, sweetener, acidulant, preservative, flavor, binder, thickener, colorant, and mixtures thereof.

Possible content of FURTHERSUBST may be from 0.025 to 25 wt %, preferably from 0.04 to 22 wt %, the wt % being based on the weight of dry CAPSSHELL.

Examples of the salt include a sodium salt, a potassium salt, an ammonium salt or a magnesium salt. Examples of the sodium salt include sodium malate, sodium citrate, disodium hydrogen phosphate, sodium dihydrogen phosphate, sodium succinate, sodium polyphosphate, sodium pyrophosphate, sodium carbonate and sodium hydrogen carbonate.

Examples of the potassium salt include dipotassium hydrogen phosphate, potassium dihydrogen phosphate, potassium acetate and potassium carbonate. Examples of the ammonium salt include ammonium chloride. Examples of the magnesium salt include magnesium chloride and magnesium sulfate.

These salts can be used singly or in combinations of two or more thereof.

The total amount of salt may be in the range of 0.5 to 30 parts by weight with respect to a total amount of 100 parts by weight of FILMPOLYM in terms of dry weight.

Examples of the gelling agent include, but are not particularly limited to, carrageenan, gellan gum, agar, pectin, gelatin, xanthan gum, locust bean gum, curdlan, alginic acid, sodium alginate, guar gum, gum Arabic, glucomannan, tamarind seed gum, furcellaran, tara gum and karaya gum.

The amount of the gelling agent to be used falls within the range of 0 to 10 wt % and preferably 0 to 5 wt %, based on the dry weight of CASPSHELL.

Examples of the plasticizer include triethyl citrate, glycerin, D sorbitol (D-sorbitol/sorbitan solution), D-mannitol, trehalose, a vegetable oil (sesame oil, castor oil), a medium chain triglyceride, a triacetin, a phthalate (dioctyl phthalate), a phytosterol, a propylene glycol, polysorbate and a polyethylene glycol (macro goal).

Examples of the pH regulator include phosphoric acid, hydrochloric acid, citric acid, glycine, gluconic acid, succinic acid, acetic acid, tartaric acid, lactic acid, fumaric acid, boric acid, maleic acid, sulfuric acid, malic acid, ammonia, a hydroxide, an amine, and salts thereof.

Examples of the sweetener include aspartame, acesulfame potassium, amacha powder, liquid sugar, fructose, glucose, reduced maltitol syrup, licorice, xylitol, glycine, glycerin, glycyrrhizinate, brown sugar, saccharin, sucralose, stevia extract, refined white sugar, purification honey, D-sorbitol, maltitol, maltose and D-mannitol.

Examples of the acidulant include adipic acid, itaconic acid, citric acid, trisodium citrate, glucono-delta-lactone, gluconic acid, potassium gluconate, sodium gluconate, succinic acid, monosodium succinate, disodium succinate, sodium acetate, tartaric acid, lactic acid, sodium lactate, acetic acid, phytic acid, fumaric acid, malic acid and phosphoric acid.

Examples of the preservative include benzoic acid, sodium benzoate, p-hydroxybenzoate, sodium sulfite, sodium hyposulfite, sodium pyrosulfite, potassium pyrosulfite, propionic acid, calcium propionate, sodium propionate, storax extract, capillary artemisia extract, Milt protein extract, a sorbic acid compound, sodium dehydroacetate, nysin, sulfur dioxide, a pectin degradation product and epsilon-polylysine.

Examples of the flavor include various essences, flavors, peppermint, menthol, peppermint, cinnamon, fennel and camphor.

The sweetener, acidulant and flavor are suitably used when FILMCOMP is used for edible products.

Examples of the thickener include alginic acid, alginate, gum Arabic, karaya gum, guar gum, gellan gum, tamarind seed gum, tara gum, tragacanth gum, carrageenan, CMC-Ca, CMC-Na, glucosamine, pullulan, pectin, sodium polyacrylate, methylcellulose, curdlan and modified starch.

The strength of a capsule film can be increased by use of the thickener and binder.

A colorant may be a dye or a pigment with a black, white, grey or any chromatic color. The term chromatic color herein refers to all colors except black, white and gray.

Further subject of the invention is a method for preparation of CASPSHELL by a process, PROCFORMCAPS;
wherein
in PROCFORMCAPS a capsule shell is formed from a solution, DIPSOL, DIPSOL is a solution of FILMPOLYM in water;
with CAPSSHELL and FLIMPOLYM as defined herein, also with all their embodiments.

PROCFORMCAPS may be any conventional process for forming capsule shells known to the skilled person, such as extrusion molding, injection molding, casting or dip molding, preferably by dip molding.

CAPSSHELL, that is the cap and the body, that is the capsule film, is formed by drying DIPSOL.

Dip molding can also be called dip coating.

The cap of CAPSSHELL made by dip molding is formed by a mold pin having the respective geometric shape complementary to the desired shape of the cap. The body of CAPSSHELL made by dip molding is formed by a mold pin having the respective geometric shape complementary to the desired shape of the body. By using the respective mold pin for the dip molding either the cap or the body is obtained.

Dip molding comprises the steps of:
1. dipping a mold pin for the first of the two parts of CAPSSHELL in DIPSOL;
2. allowing a film to form on the mold pin after the dipping to provide a film on the mold pin;
3. drying said film on the mold pin providing said first part of CAPSSHELL; and
4. removing said first part of CAPSSHELL shell from the mold pin;
5. repeating the steps 1 to 4 with the mold pin for the second part of CAPSSHELL; with DIPSOL as defined herein, also with all its embodiments.

Step 2 and step 3 may be done simultaneously.

After the preparation of both parts of CAPSSHELL, both parts may be telescopically engaged with each other to form the capsule.

The part of a capsule shell which is removed from the mold pin may have a size which is still longer then the target length of the desired part of a capsule shell, in this case the part of the capsule shell on the mold pin and after removal from the mold pin represents a green body or can also be called an un-machined part, and is cut to the desired length to provide the desired part of a capsule shell in the desired length.

The mold pin may have a temperature, PINTEMP, for the dip molding. In one embodiment the mold pin has PINTEMP when it is dipped into DIPSOL and while the film is dried on the mold pin after the dipping.

PINTEMP may be from ambient temperature to 60° C.

The temperature of DIPSOL during the dipping of the mold pin into DIPSOL may be from ambient temperature to 75° C., preferably from 20 to 75° C., more preferably from 20 to 70° C., even more preferably from 20 to 65° C.

Drying of the film on the mold pin may be done by air drying. Drying may be done at elevated temperature.

The temperature for drying of the film on the mold pin may be from ambient temperature to 60° C., preferably from 20 to 60° C.

After the joining of both parts to form the capsule, CAPSSHELL may be further dried; this drying may be done at a temperature of from ambient temperature to 60° C.

The typical wall thickness of CAPSSHELL made by dip molding is essentially the same for every segment or part of CAPSSHELL, of the cap and of the body.

DIPSOL may be prepared by a dissolution, DISSOL, of FILMPOLYM in water.

DIPSOL may further comprise FURTHERSUBST; which may be mixed with the water before the dissolution FILMPOLYM in the water, or it may be mixed with the solution of FILMPOLYM in water.

DIPSOL comprises FILMPOLYM and any FURTHERSUBST in amounts based on the dry weight of DIPSOL which are equal to the amounts of FILMPOLYM and of any FURTHERSUBST in FILMCOMP, that is in CAPSSHELL, based on the dry weight of CAPSSHELL.

The amounts FILMPOLYM and of any FURTHERSUBST are calculated and chosen in such a way that the desired amounts of FLIMPOLYM and of any FURTHERSUBST in DIPSOL is provided in order to provide for the desired amounts of FILMPOLYM and of any FURTHERSUBST in FILMCOMP, that is in CAPSSHELL.

The amounts of FILMPOLYM and of any FURTHERSUBST in dry DIPSOL is equal to the respective amounts in dry FILMCOMP, that is in dry CAPSSHELL.

Further subject of the invention is CAPSSHELL filled with a formulation, FILLFORMUL, comprising an ingredient, INGR, INGR may be an active pharmaceutical ingredient, API, a medicament, a nutritional supplement, a nutraceutical, a vitamin, a mineral, a cosmetic, a health food or a mixture thereof;
with CAPSSHELL as defined herein, also with all its embodiments.

Further subject of the invention is the use of CAPSSHELL for filling with FILLFORMUL, with CAPSSHELL and FILLFORMUL as defined herein, also with all its embodiments.

FILLFORMUL may comprise INGR in an amount from 0.05 to 100 wt %, preferably from 0.5 to 90 wt %, more preferably from 1 to 50 wt %, even more preferably from 5 to 30 wt %, the wt % being based on the total dry weight of FILLFORMUL.

Examples for medicaments or for API are dihydropyridine derivatives (e.g., nifedipine), antiviral HIV protease inhibitors (e.g., Ritonavir, Saquinavir), therapeutic agents for hyperlipidemia (e.g., clofibrate), iodine compounds (e.g., sodium iopodate, sodium iodide), polyunsaturated fatty acid derivatives (e.g., ethyl eicosapentaenoic acid (EPA), docosahexaenoic acid (DHA)), carotenoids (e.g., lycopene, bixin, β-carotene, xanthophyll, lutein), ubiquinones (coenzyme Q) (e.g., ubidecarenone used as a metabolizable cardiac stimulant), various vitamin derivatives, as well as indomethacin, colchicine, diazepam, syrosingopine, norethisterone, piretanide, propericyazine, perphenazine, mequitazine, medazepam, menatetrenone, indenolol hydrochloride, reserpine, sofalcone, bromocriptine mesilate, bufetolol hydrochloride and oxprenolol hydrochloride. Among vitamin derivatives, fat soluble ones are preferred for use. Examples include vitamin A derivatives (e.g., tretinoin, liver oil, retinol palmitate), vitamin A analogs (e.g., etretinate), vitamin D derivatives, vitamin E derivatives (e.g., tocopherol nicotinate, tocopherol acetate, tocopherol calcium succinate), or vitamin K derivatives (e.g., phytonadione (vitamin K1), menaquinone (vitamin K2), menadione (vitamin K3), menatetrenone, phytonadione).

A medicament or an API as INGR can be filled into CAPSSHELL either alone or in combination with any base or carrier, additive, or excipient. Any type of base or carrier, either fat-soluble or water-soluble, can be used as long as it does not impair the medicament's or API's activity and does not affect various physical properties of CAPSSHELL, such as strength, gas permeability, and disintegration or dissolution profiles. Likewise, the base per se may be in a liquid or solid state at normal temperature as long as it can be filled into CAPSSHELL with the help of heating or dilution with other solvents, etc. Examples of such a base include vegetable oils (e.g., soybean oil, sesame oil, cottonseed oil, olive oil), fatty acid glycerides (e.g., medium chain triglycerides), propylene glycol, propylene glycol fatty acid esters, polyethylene glycol, polyvinylpyrrolidone, triacetin, liquid paraffin, polyoxyethylene sorbitan fatty acid esters, sucrose fatty acid esters, ethanol and purified water, which may be used alone or in combination. Bases preferred for dissolving fat-soluble medicaments or APIs such as vitamins A, D, E and K are vegetable oils or fatty acid glycerides, with medium chain triglycerides being particularly preferred. In the case of using a water-soluble base, it is preferable to provide a protection layer between the capsule shell layer and the medicament or API layer or a crystallization inhibitor in consideration of influences on CAPSSHELL A medicament or API to be filled into CAPSSHELL of the present invention is preferably exemplified by, but not limited to, those in a liquid form or those dissolved, suspended or emulsified in such a base as listed above. The medicament or API may also be in a solid form (e.g., powders, granules) or in a semi-solid form (e.g., creams or gels).

BRIEF DESCRIPTION OF THE DRAWINGS

The present invention will be described again with reference to the enclosed drawings, wherein.

DETAILED DESCRIPTION OF PREFERRED EMBODIMENTS

Figure 1:
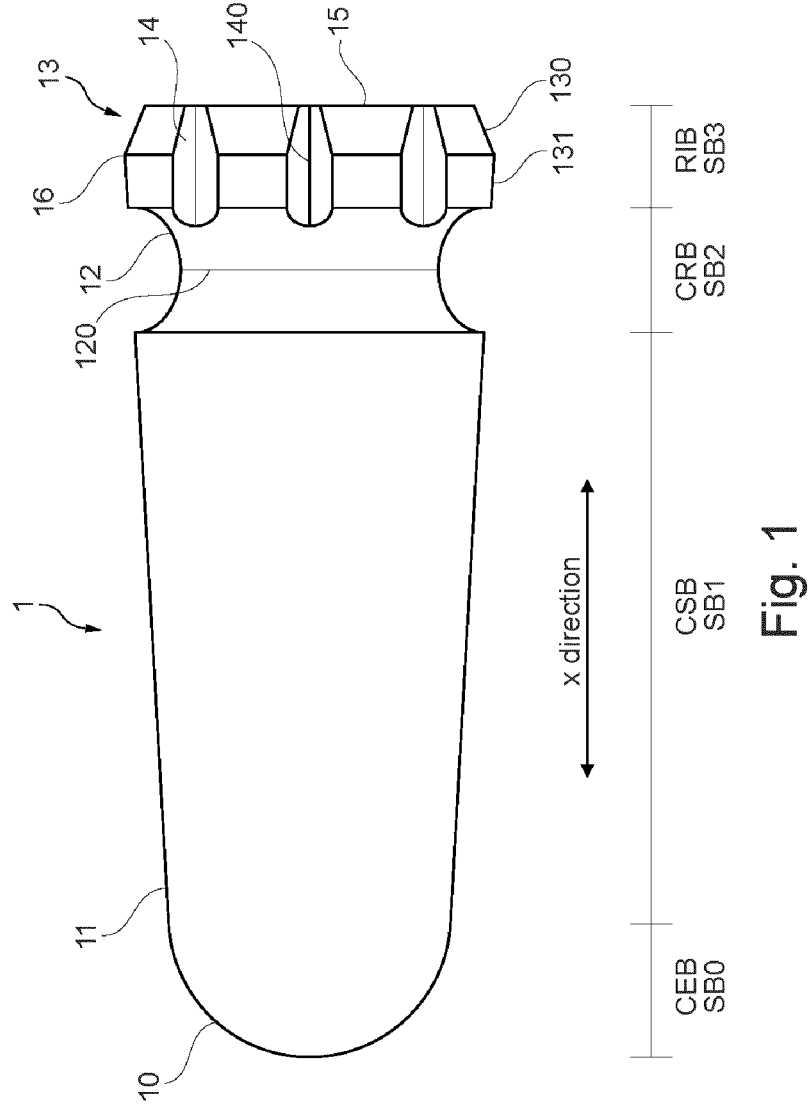
FIG. 1: shows a schematic sectional side view of a first embodiment of a body of CAPSSHELL.

The present invention will now be described in more detail with reference to the enclosed figures. Same components and arrangements are denoted in the figures by the same reference numerals and the respective description may be omitted in order to avoid redundancies.

FIG. 1 shows one embodiment of a body 1 having four segments CEB 10, CSB 11, CRB 12 and RIB 13.

CEB 10 is dome shaped. CSB 11 is a hollow-cylindrical segment of the body with a taper, the taper increases the diameter of CSB 11 from the closed end CEB 10 towards the open end of the body. CRB 12 extends over the entire circumference of the body. Its cross section in x direction has a U shape. Line 120 indicates the lowest path of CRB 12, that is the line where the indentation of CRB 12 has the largest depth. RIB 13 has AVs 14. FIG. 1 shows three AVs 14. Line 140 indicates the lowest path of AV 14, that is the line where the indentation of AV 14 has the largest depth. RIB 13 has two segments RIBO 130 and RIBC 131, RIBO 130 is the segment of RIB 13 towards the open end of the body, RIBC 131 is the segment of RIB 13 towards the closed end of the body. RIBO 130 has a taper in x direction, thereby the diameter of RIBO 130 is reduced in x direction towards the open end of the body. Also RIBC 131 has a taper in x direction, thereby the diameter of RIBC 131 is reduced in x direction towards the closed end of the body. Where RIBO 130 transitions to RIBC 131, the diameter of RIBO 130 and of RIBC 131 are identical, so there is no step in diameter between RIBO 130 and RIBC 131. EB 15 is the edge of the open end of the body. MDB 16 is the diameter where RIBO 130 and RIBC 131 connect to each other. The AVs 14 of the RIB 13 extend from the EB 15 over the full length of RIB 13 to the beginning of CRB 12.

The inclination of the taper of CSB 11 and of RIBC 131 are the same. The area of RIBC 131 is an extension of the area of CSB 11.

Figure 2:
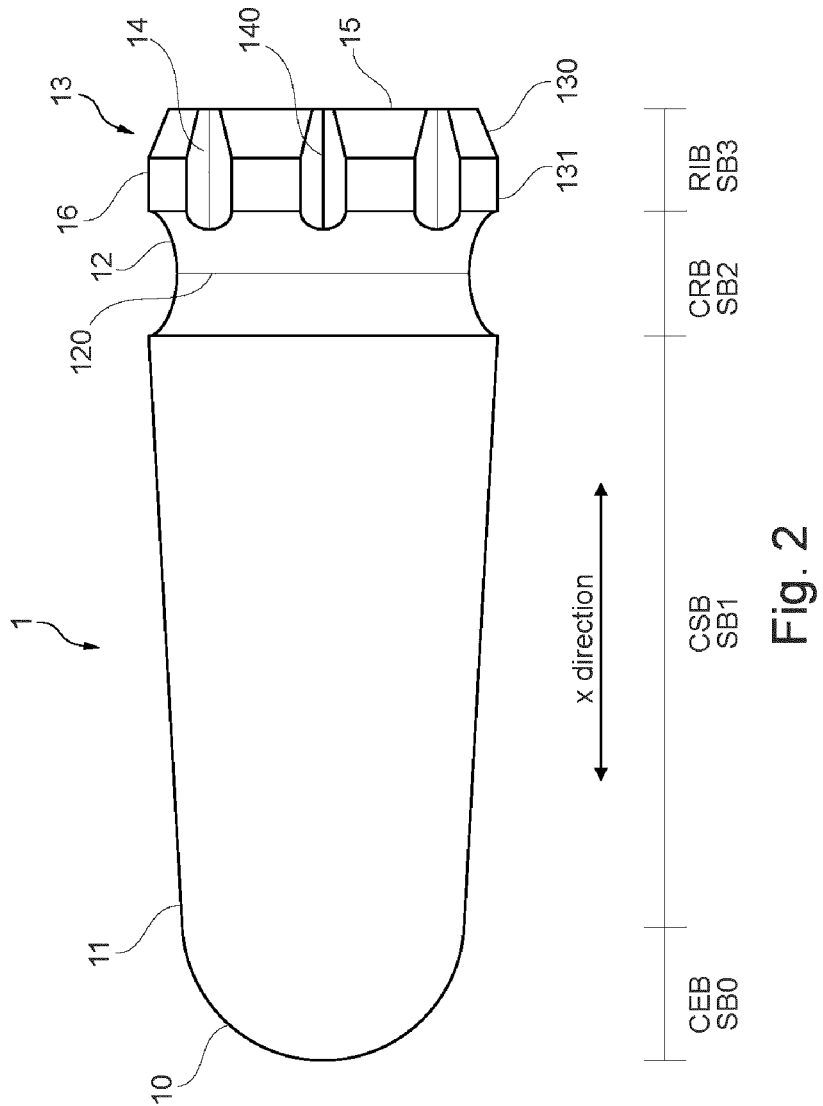
FIG. 2: shows a schematic sectional side view of a second embodiment of a body of CAPSSHELL.

FIG. 2 shows another embodiment of a body 1 having four segments CEB 10, CSB 11, CRB 12 and RIB 13.

CEB 10 is dome shaped. CSB 11 is a hollow-cylindrical segment of the body with a taper, the taper increases the diameter of CSB 11 from the closed end towards the open end of the body.

CRB 12 extends over the entire circumference of the body. Its cross section in x direction has a U shape. Line 120 indicates the lowest path of CRB 12, that is the line where the indentation of CRB 12 has the largest depth. RIB 13 has AVs 14. FIG. 1 shows three AV 14. Line 140 indicates the lowest path of AV 14, that is the line where the indentation of AV 14 has the largest depth. RIB 13 has two segments RIBO 130 and RIBC 131, RIBO 130 is the segment of RIB towards the open end of the body, RIBC 131 is the segment of RIB 13 towards the closed end of the body. RIBO 130 has a taper in x direction, thereby the diameter of RIBO 130 is reduced in x direction towards the open end of the body. RIBC 131 has no taper in x direction, thereby the diameter of RIBC 131 is the same over its entire length. Where RIBO 130 and RIBC 131 transition from one to the other the diameter of RIBO 130 and of RIBC 131 are identical, so there is no step in diameter between RIBO 130 and RIBC 131. EB 15 is the edge of the open end of the body. MDB 16 is the diameter of RIBC 131.

The diameter of the edge of RIBC 131 is an extrapolation of the growing diameter of CSB 11 in x direction. So the diameter of the edge of RIBC 131 is the same as the diameter of the edge of CSB 11 towards the open end of the body.

Figure 3:
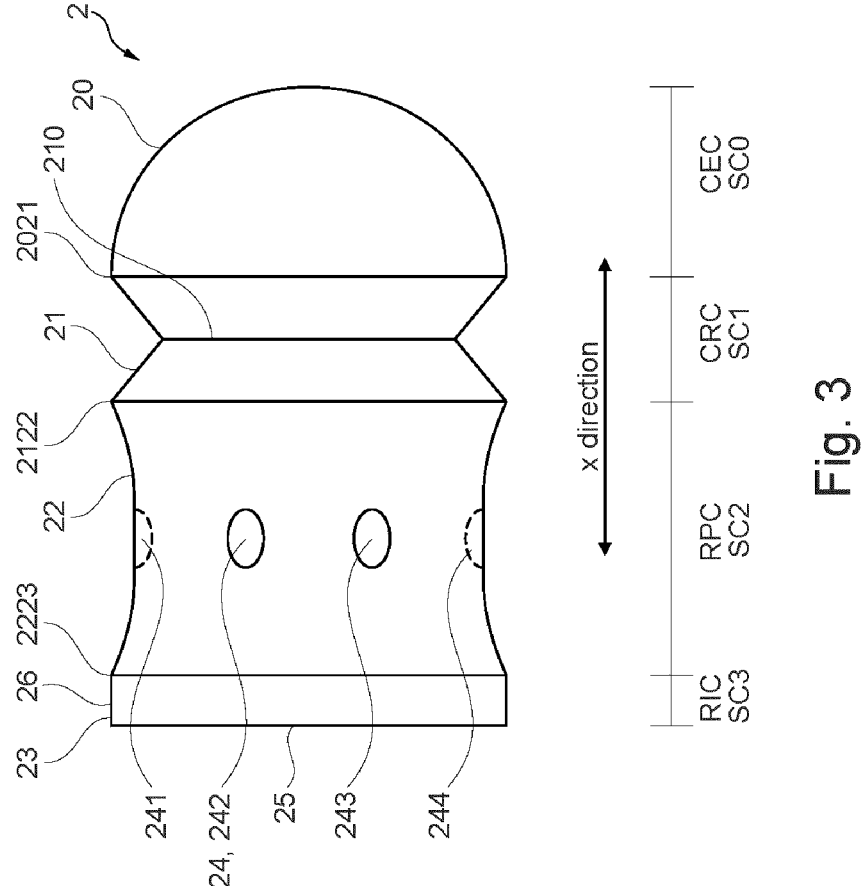
FIG. 3: shows a schematic sectional side view of a first embodiment of a cap of CAPSSHELL.

FIG. 3 shows one embodiment of a cap 2 having four segments CEC 20, CRC 21, RPC 22 and MC 23.

CEC 20 is dome shaped. CRC 21 is a closure ring of the cap extending over the entire circumference of the cap 2. The cross section in x direction of CRC 21 is V shaped. The line 210 indicates the lowest path of CRC, that is the line where the indentation of CRC 21 has the largest depth. The cross section in x direction of RPC 22 is U shaped. RPC 22 has protrusion PRPC 24. FIG. 1 shows 4 PRPC 24, the two in the middle (PRPC 242 and PRPC 243) are shown in side view, the one on top (PRPC 241) and the one at the bottom (PRPC 244) are shown as cross sections in x direction. PRPC 241 and PRPC 242 are on diametrical opposite sides of the cap to each other. Not shown are two further PRPC which are on the diametrical opposite sides to PRPC 242 and PRPC 243 respectively. So in total the cap 2 shown in FIG. 3 has six PRPCs 24. The area of PRPCs 24 is of oval shape with the length being larger than the width. The cross section in x direction of PRPCs 24 is U shaped. The PRPCs 24 are located over the circumference of the cap 2, they are separated by parts of RPC 22 and they have equal distance from each other. PRPCs 24 all have the same distance from EC 25. The PRPCs 24 are located in the middle of RPC 22 with respect to the x direction. MC 23 has no taper, so the diameter of MC 23 is the same over the length of MC 23.

D-CEC-CRC 2021, the diameter of CEC 20 and CRC 21 at the transition from CEC 20 to CRC 21, D-CRC-RPC 2122, the diameter of CRC 21 and RPC 22 at the transition from CRC 21 to RPC 22, D-RPC-MC 2223, the diameter of RPC 22 and RIC 23 at the transition from RPC 22 to RIC23, are respectively identical, so there is no step wise change of diameter between CEC 20 and CRC 21, between CRC 21 and RPC 22 and between RPC 22 and RIC 23, they are MDC 26.

Figure 4:
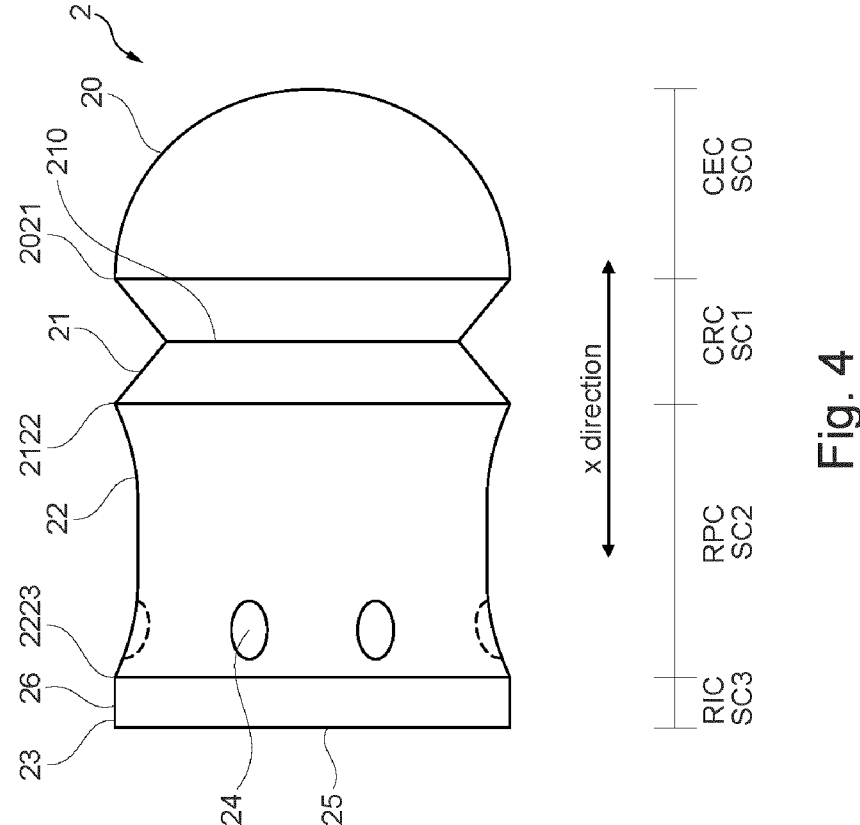
FIG. 4: shows a schematic sectional side view of a second embodiment of a cap of CAPSSHELL.

FIG. 4 shows another embodiment of a cap 2; this embodiment is identical to the embodiment shown in FIG. 3 with the exception, that the PRPC 24 are located in first third of the length of RPC 22 with respect to the x direction from the EC 25.

Figure 5:
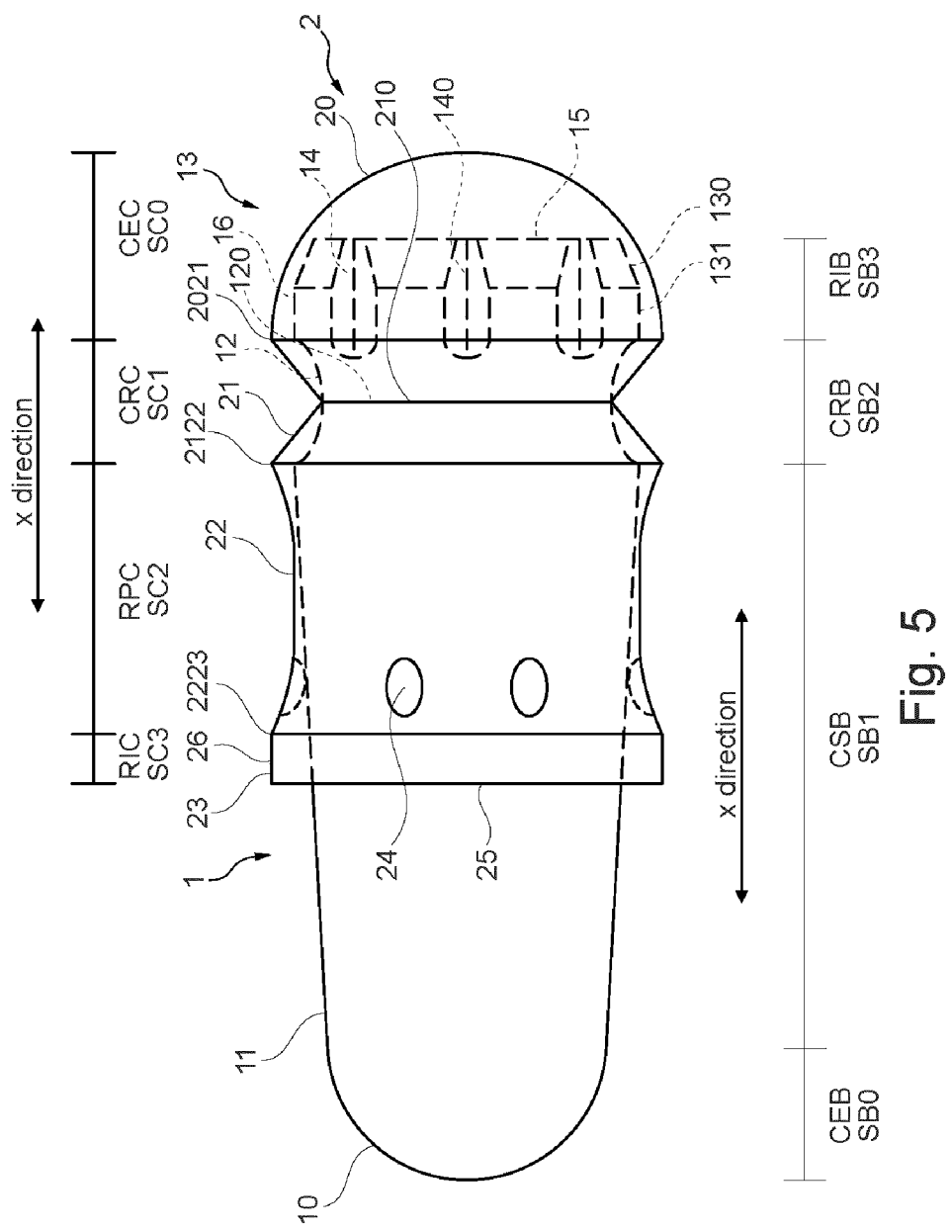
FIG. 5: shows an overlay of overlay of FIG. 4 over FIG. 2 in the closed position.

FIG. 5 shows an overlay of overlay of FIG. 4 over FIG. 2 in the closed position. The cap 20 is telescopically engaged with the body 10. CAPSSHELL is in the closed position. PRPC 24 engage with CSB 11. CRC 21 engages with CRB 12.

Figure 6:
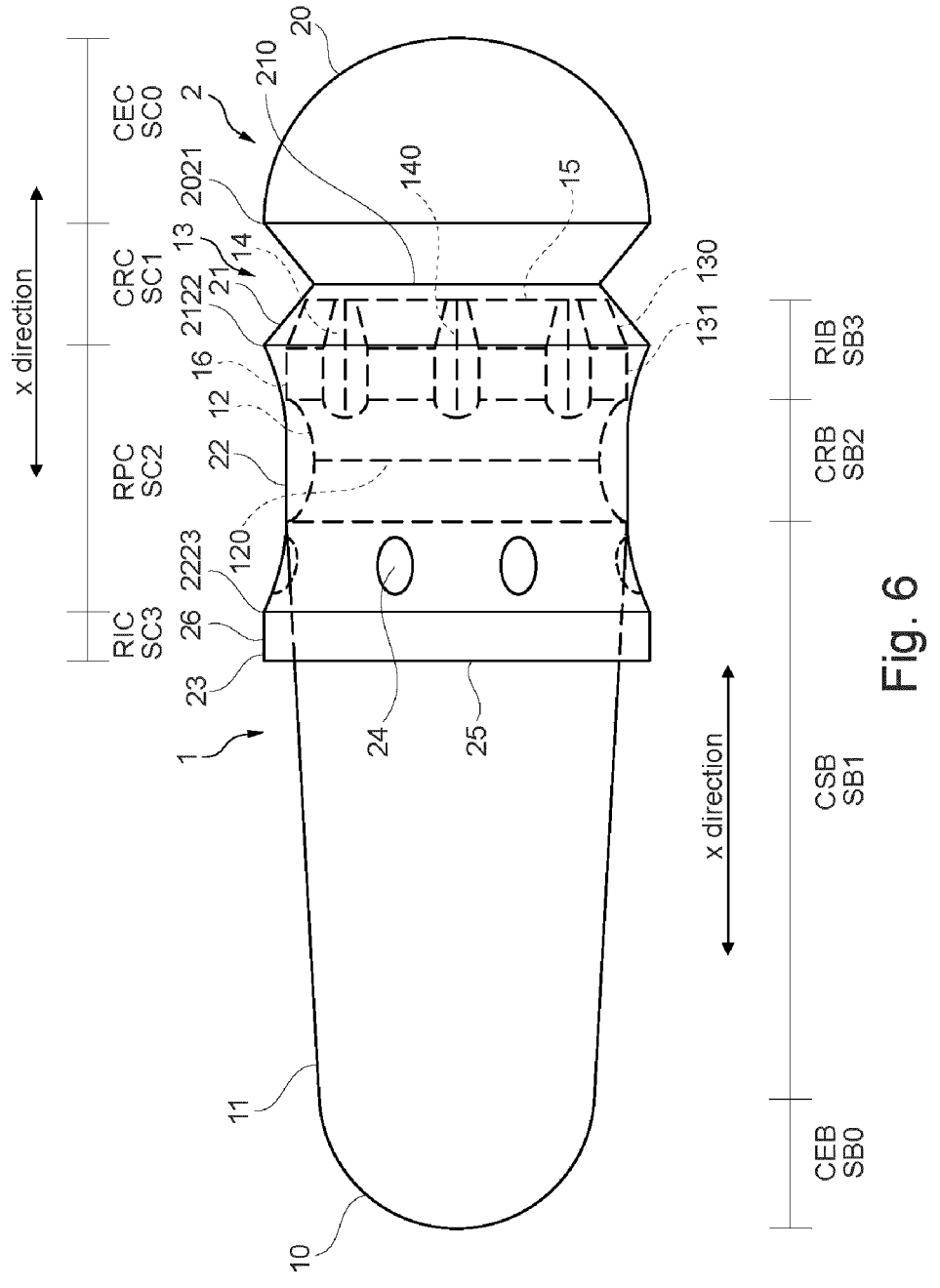
FIG. 6: shows an overlay of overlay of FIG. 4 over FIG. 2 in the preclosed position.

FIG. 6 shows an overlay of overlay of FIG. 4 over FIG. 2 in the preclosed position. The cap 20 is telescopically engaged with the body 10. CAPSSHELL is in the preclosed position. PRPC 24 engage with CSB 11. CRC 21 is on the other side of RIB 13 with respect to CRB 12, that is CRC 21 is on the open end side of RIB 13.

Figure 7:
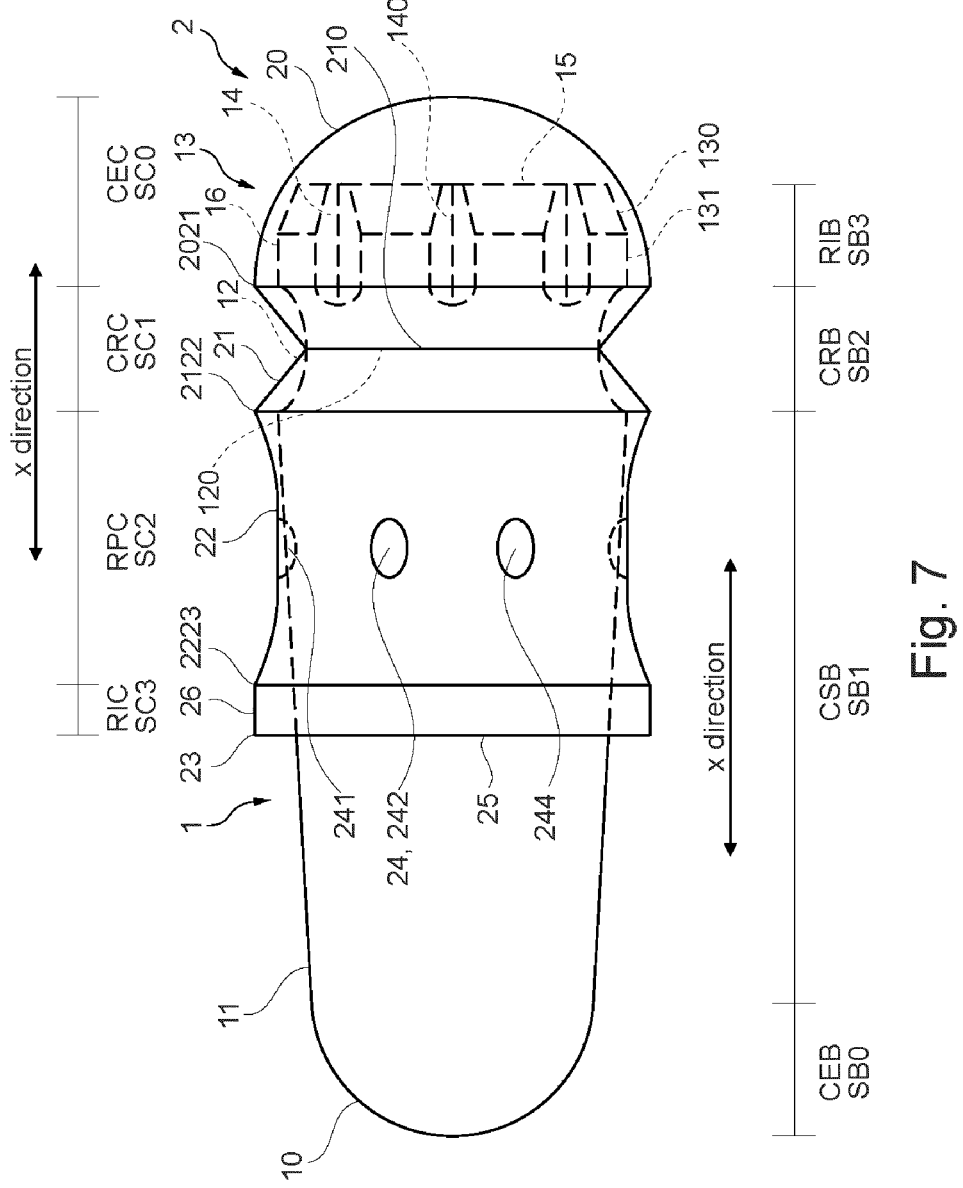
FIG. 7: shows an overlay of overlay of FIG. 3 over FIG. 2 in the closed position.

FIG. 7 shows an overlay of overlay of FIG. 3 over FIG. 2 in the closed position. The cap 20 is telescopically engaged with the body 10. CAPSSHELL is in the closed position. PRPC 24 engage with CSB 11. CRC 21 engages with CRB 12.

Figure 8:
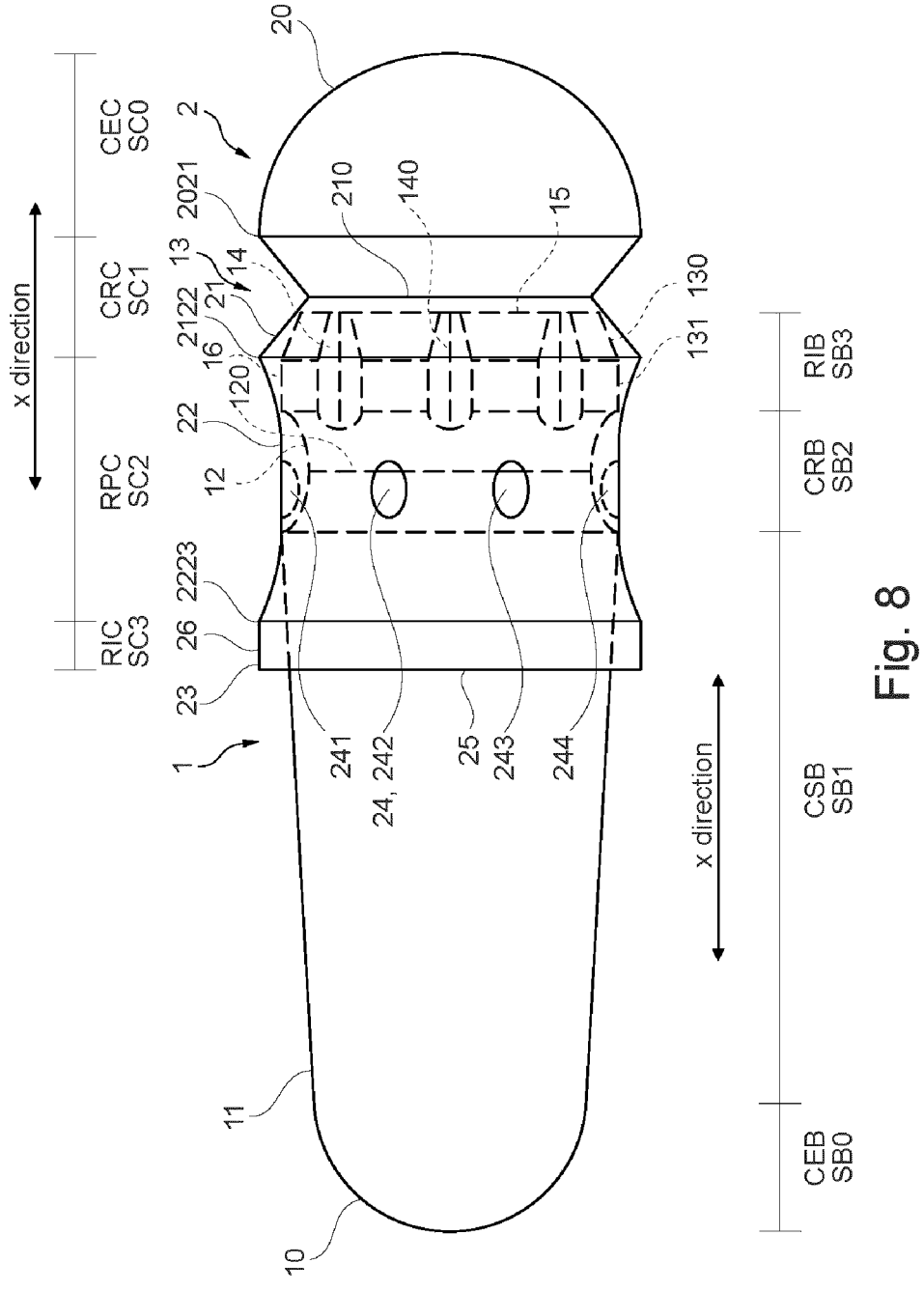
FIG. 8: shows an overlay of overlay of FIG. 3 over FIG. 2 in the preclosed position.

FIG. 8 shows an overlay of overlay of FIG. 3 over FIG. 2 in the preclosed position. The cap 20 is telescopically engaged with the body 10. CAPSSHELL is in the preclosed position. PRPC 24 engage with CRB 12. CRC 21 is on the other side of RIB 13 with respect to CRB 12, that is CRC 21 is on the open end side of RIB 13.

Figure 9:
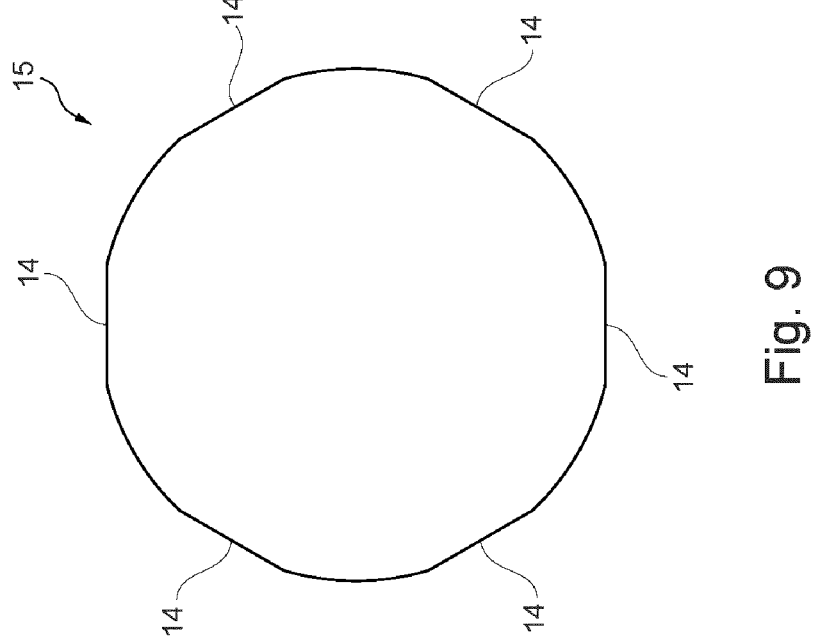
FIG. 9: shows a top view of the EB.

FIG. 9 shows a top view of the EB 15 with six AVs 14. The EB 15 is the cutting edge of the RIB 13. The recesses formed by the AVs 14 have flat bottoms. The six AVs 14 are three pairs of AVs 14 wherein the AVs 14 of each pair are located on diametrical opposite sides of each other on the EB 15. The size and the shape of the AVs 14 are identical. All six AVs 14 are separated by parts of the RIB 13 with equal width, thereby the AVs 14 are placed with equal distance from each other over the circumference of the RIB 13.

EXAMPLES

Two designs D1 and D2 are exemplified with the following dimensions and characteristics.
The wall thickness of D1 and of D2, that is the wall thickness of the capsule film, is about 105 micrometer.
The capsule size of D1 and of D2 is size 0 as disclosed in the Technical Reference File Hard Gelatin Capsules, 2nd Edition, Capsugel Library, www.capsugel.com.
In the closed position D1 and D2 have an essentially hollow-cylindrical shape, except for CEC and CEB which are dome shaped.

The PLF for D1 and D2 was 0.15 N on average.
The SFF for D1 and D2 was 5 N on average.
Dimensions of Cap:
The inner length of the cap, that if from the inner surface of CEC to the cutting edge of RIC, was 10'600 micrometer for D1 and for D2.
MDC for D1 and for D2 was 7'440 micrometer.
Table 1 gives the length of the segments in percent of the length of the cap, the percentages add up to 100%.

TABLE 1

| | [%] D1 | [%] D2 |
|---|---|---|
| CEC | 40 | 40 |
| CRC | 15 | 15 |
| RPC | 36 | 36 |
| RIC | 9 | 9 |

Further dimensions of cap:
DCRC: 96.3% of MDC for D1 and for D2
DRPC: 0.66% of MDC for D1 and for D2
DPRPC: 98.2% of MDC for D1, 98.3% of MDC for D2
Length of the PRPC: 25% of length of RPC for D1, 23% of length of RPC for D2
Width of PRPC relative to their length: 86% for D1; 87% for D2
Position of PRPC in the RPC:
D1: in the quarter of the length extension of the RPC closest to the RIC
D2: the centers of the PRPCs are located at the middle of the length of the RPC
The maximum depth of the indentation formed by the PRPC: 70 micrometers for D1, 65 micrometers for D2
D1 and D2:
The RPC has 6 PRPCs.
All the PRPCs are identical in shape and depth.
The PRPCs are placed with equal distance from each other over the circumference of the RPC. The PRPC are placed in such a way that always two PRPC form a pair that are located on diametric opposite sides of the PRC.
D-CEC-CRC, D-CRC-RPC and D-RPC-RIC are identical to MDC.
RPC extends over the entire circumference of the cap.
Dimensions of body:
The outer_length of the body, that is from outer surface of CEB to the cutting edge of RIB, was 18'440 micrometers for D1 and for D2.
MDB was 7'325 micrometer for D1 and for D2.
Table 2 gives the length of the segments in percent of the length of the body, the percentages add up to 100%.

TABLE 2

| | [%] D1 | [%] D2 |
|---|---|---|
| combined length of CEB and CSB | 89 | 89 |
| CRB | 5 | 5 |
| RIB | 6 | 6 |

Further dimensions of body:
DCRB: 97.9% of MDB for D1 and for D2
AV:
DAV: 99.6% of MDB for D1 and for D2
D1 and D2: The RIB has 8 AVs placed with equal distance from each other over the circumference of the RIB in such a way that always two of the AVs form a pair that are located on diametrical opposite sides of the RIB The shape of the area of the AV and the depth of the indentation formed by the AV are the same for each AV, that means all the AV are identical, that means the shape and the depth of all of the AVs are identical.

The length of the AVs is the same as the length of the RIB, thereby the AVs extends from the EB to the CRB.

The outer diameter of the CRB at the transition from the RIB to the CRB is the same as the outer diameter of the RIB at this transition, that means the outer diameter does not make a step wise change at the transition between the RIB and the CRB.

The AVs extend into the CRB until the point where the depth of the protrusion of the AV is equal to the depth of the protrusion of the CRB.

The width of AVs is 90% of the length of the AVs.

D1 and D2:

RIB is divided into RIBO with a length of 450 micrometer and RIBC with a length of 600 micrometer; RIBO has a taper with an inclination of 23°, thereby reducing the diameter by 36 micrometer.

The diameter of the CRB and the diameter of the RIB are equal at the transition from the CRB to the RIB.

The diameter of the CSB and the diameter of the CRB are equal at the transition from the CSB to the CRB.

Interference Between Cap and Body

The shape of RPC over its length is a concave shape for D1 and for D2.

The depth of the gap formed between RPC and the point of the body with the MDB which is called clearance is 10 micrometers for D1 and for D2.

IDPRPC: 22 micrometer for D1, 27 micrometer for D2

Relative Locations:

D1: PRPC engage in the preclosed position with CSB. In the preclosed position CRC is on the other side of RIB with respect to CRB, that is CRC is on the open end side of RIB. The PRPCs are arranged in the RPC at a distance in x direction from the position of the smallest diameter of the CRC which distance is larger than the distance in x direction between the EB and the end of the CRB adjacent to the CSB.

D2: PRPC engage in the preclosed position with CRB. In the preclosed position CRC is on the other side of RIB with respect to CRB, that is CRC is on the open end side of RIB. The PRPCs are arranged in the RPC at a distance in x direction from the position of the smallest diameter of the CRC which distance equals the distance in x direction between the EB and the position of the smallest diameter of the CRB.

D1 is displayed schematically in FIG. 5 and FIG. 6, the cap of D1 is schematically displayed in FIG. 4, the body of D1 is schematically displayed in FIG. 2.

D2 is displayed schematically in FIG. 7 and FIG. 8, the cap of D2 is schematically displayed in FIG. 3, the body of D2 is schematically displayed in FIG. 2.

D1 and D2:

In the closed position the PRPCs engage with CSB.

In the closed position CRC engages with CRB.

LIST OF REFERENCE NUMERALS 1 body
10 CEB
11 CSB
12 CRB
120 line indicating lowest path of CRB

22

13 RIB
130 RIBO
131 RIBC
14 AV
140 line indicating lowest path of AV
15 EB
16 MDB
2 cap
20 CEC
2021 D-CEC-CRC
21 CRC
210 line indicating lowest path of CRC
2122 D-CRC-RPC
22 RPC
2223 D-RPC-RIC
23 RIC
24, 241, 242, 243, 244 PRPC
25 EC
26 MDC

The invention claimed is:

1. A telescope-type capsule shell, which is CAPSSHELL, with two separate parts, a cap (2) and a body (1), wherein the cap (2) and the body (1) telescopically engage with each other for closing CAPSSHELL;

the cap (2) has a closed end, which is CEC (20), and an open end comprising a rim;

the body (1) has a closed end, which is CEB (10), and an open end comprising a rim;

the cap (2) comprises in the x direction four consecutive segments: segment of the cap 0, which is SC0, segment of the cap 1, which is SC1, segment of the cap 2, which is SC2 and segment of the cap 3, which is SC3;

SC0 comprises CEC (20);

SC1 comprises a closure ring of the cap (2), which is CRC (21), in form of a protrusion that extends over the entire circumference of the cap (2);

SC2 comprises a region of protrusion of the cap (2), which is RPC (22);

SC3 comprises the rim of the open end of the cap (2), which is RIC (23);

the body (1) comprises in the x direction four consecutive segments: segment of the body 0, which is SB0, segment of the body 1, which is SB1, segment of the body 2, which is SB2 and segment of the body 3, which is SB3;

SB0 comprises CEB (10);

SB1 comprises a hollow-cylindrical segment of the body (1), which is CSB (11);

SB2 comprises a closure ring of the body (1), which is CRB (12), in form of a protrusion that extends over the entire circumference of the body (1);

SB3 comprises the rim of the open end of the body (1), which is RIB (13);

in the RPC (22) there are at least two protrusions, which are PRPC (24), and which are separated from each other in the circumferential direction of the cap (2) by parts of RPC (22);

a closed position is the position where the cap (2) is fully engaged with the body (1) so that CASPSHELL is closed, in the closed position CRC (21) engages with CRB (12);

any protrusion of CAPSSHELL extends inwardly into the cavity of the cap (2) or the body (1), respectively;

the extension of the CAPSSHELL, when the cap (2) is telescopically engaged with the body (1) in the direction of its length is designated as x direction;

characterized in that in the RIB (13) there are at least two airvents, which are
AV (14), in form of protrusions, and which are sepa-
rated from each other and which extend from the edge
of the open end of the body (1), which is EB (15), to the
CRB (12), but not over the entire length of the CRB
into the CSB;

and the RPC (22) extends over the entire circumference of
the cap (2).

2. CAPSSHELL according to claim 1, wherein
the maximum inner diameter of the cap (2), which is
MDC (26), is the largest inner diameter of the RIC (23).

3. CAPSSHELL according to claim 1, wherein
the maximum outer diameter of the body (1), which is
MDB (16), is the largest outer diameter of the RIB (13).

4. CAPSSHELL according to claim 1, wherein
PRPC (24) engage in a preclosed position with CSB (11).

5. CAPSSHELL according to claim 1, wherein
when CAPSSHELL is in a preclosed position, CRC (21)
is on the other side of RIB (13) with respect to CRB
(12).

6. CAPSSHELL according to claim 1, wherein
the PRPCs (24) are arranged in the RPC (22) at a distance
in x direction from the position of the smallest diameter
of the CRC (21) which distance is larger than the
distance in x direction between the EB (15) and the end
of the CRB (12) adjacent to the CSB (11).

7. CAPSSHELL according to claim 1, wherein
PRPC (24) engage with CRB (12) in a preclosed position
of CAPSSHELL.

8. CAPSSHELL according to claim 7, wherein
when CAPSSHELL is in a preclosed position, CRC (21)
is on the other side of RIB (13) with respect to CRB
(12).

9. CAPSSHELL according to claim 1, wherein
the PRPCs (24) are arranged in the RPC (22) at a distance
in x direction from the position of the smallest diameter
of the CRC (21) which distance equals the distance in
x direction between the EB (15) and the position of the
smallest diameter of the CRB (12).

10. CAPSSHELL according to claim 1, wherein
the shape of a longitudinal cut in x direction of the
indentation that the RPC (22) forms is a curved shape.

11. CAPSSHELL according to claim 1, wherein
between the RPC (22), except for any area formed by the
PRPC (24), and the circumference of the body (1) with
MDB (16) there occurs no interference during the
telescopic engagement of the cap (2) with the body (1);
interference means that the diameter between two dia-
metrically opposing points of the inner surface of the
cap (2) is smaller than the MDB (16).

12. CAPSSHELL according to claim 1, wherein
between the PRPC (24) and the circumference of the body
(1) with MDB (16) there occurs an interference during
the telescopic engagement of the cap (2) with the body
(1) such that PRPC (24) engages in a preclosed position
with CRB.

13. CAPSSHELL according to claim 1, wherein
the RPC (22) has 2, 3, 4, 5, 6, 7, 8, 9 or 10 PRPC (24).

14. CAPSSHELL according to claim 1, wherein
the PRPCs (24) are placed with equal distance from each
other over the circumference of the RPC (22).

15. CAPSSHELL according to claim 1, wherein
all the PRPCs (24) are identical in shape and depth.

16. CAPSSHELL according to claim 1, wherein
the PRPCs (24) are separated in x direction from the
beginning and the end of RPC (22) by parts of RPC
(22).

17. CAPSSHELL according to claim 1, wherein
all the PRPCs (24) have the same distance from RIC (23)
in x direction.

18. CAPSSHELL according to claim 1, wherein
the shape of a longitudinal cut in x direction of the CRC
(21) has an U shape or a V shape.

19. CAPSSHELL according to claim 1, wherein
during the telescopic engagement of the cap (2) with the
body (1) an interference, which is ICRC, occurs
between CRC (21) and RIB (13) during the telescopic
engagement of the cap (2) with the body (1).

20. CAPSSHELL according to claim 1, wherein
in the closed position, CRC (21) engages with CRB (12)
with an interference.

21. CAPSSHELL according to claim 1, wherein
in the closed position the PRPCs (24) engage with CSB
(11).

22. CAPSSHELL according to claim 1, wherein
the RIB (13) has two adjacent segments over its length,
one segment, which is RIBO (130), towards the open
end of the body (1) and one segment, which is RIBC
(131), towards the closed end of the body (1); RIBO
(130) has a taper by which the diameter of RIB (13) is
reduced over the length of the RIBO (130) towards EB
(15).

23. CAPSSHELL according to claim 1, wherein
the RIB (13) has 2, 3, 4, 5, 6, 7, 8, 9, 10, 11 or 12 AVs (14).

24. CAPSSHELL according to claim 1, wherein
the AVs (14) are placed with equal distance from each
other over the circumference of the RIB (13).

25. CAPSSHELL according to claim 1, wherein
the shape and the depth of all of the AVs (14) are identical.

26. CAPSSHELL according to claim 1, wherein
the shape of a longitudinal cut in x direction of the CRB
(12) has an U shape or a V shape.

27. CAPSSHELL according to claim 1, wherein
the cap (2) and the body (1) of CAPSSHELL are each
formed by an elastic wall.

28. The CAPSSHELL according to claim 1, wherein
CASPSHELL is made of a capsule film which has a
composition, which is FILMCOMP, comprising a film-
forming polymer, which is FILMPOLYM, selected
from the group consisting of a cellulose derivative,
gelatin, pullulan, soluble starch, and a soluble starch
derivative.

29. CAPSSHELL according to claim 1, wherein CAPS-
SHELL is a hard capsule shell.

30. A method for preparation of CASPSHELL by a
process, which is PROCFORMCAPS;
wherein
in PROCFORMCAPS a capsule shell is formed from a
solution, which is DIPSOL, wherein DIPSOL is a
solution of FILMPOLYM in water;
with CAPSSHELL as defined in claim 1 and FILM-
POLYM; and
wherein FILMPOLYM comprises a film-forming polymer
selected from the group consisting of a cellulose
derivative, gelatin, pullulan, soluble starch, and a
soluble starch derivative.

31. A CAPSSHELL filled with a formulation, which is
FILLFORMUL, comprising an ingredient, which is INGR,
wherein INGR may be an active pharmaceutical ingredient, API, a medicament, a nutritional supplement, a nutraceutical, a vitamin, a mineral, a cosmetic, a health food or a mixture thereof;

with CAPSSHELL as defined in claim 1.

* * * * *